United States Patent [19]
Grenfell et al.

[11] 3,943,914
[45] Mar. 16, 1976

[54] REMOTE-RECORDING PERIODONTAL DEPTH PROBE

[76] Inventors: James W. Grenfell, 4808 SW. 35th Place, Portland, Oreg. 97221; Fred M. Sorenson, 1193 Troon Road, Lake Oswego, Oreg. 97034; Hiroshi Ueno, 3900 SW. Condor Ave., Portland, Oreg. 97201; Masato Miyahara, 302 A34 To Otokoyamadanchi, 19 Nagatani Yahataso, Yahata Cho, Tsuzukigun, Kyoto, Japan

[22] Filed: Aug. 1, 1974

[21] Appl. No.: 493,541

[30] Foreign Application Priority Data
Aug. 6, 1973  Japan.............................. 48-88229

[52] U.S. Cl. ................. 128/2 S; 32/40 R; 33/174 D
[51] Int. Cl.² .......................................... A61B 5/10
[58] Field of Search............. 128/2 S, 2 R; 32/40 R; 33/174 D, 172 E, 169 B; 346/33 ME

[56] References Cited
UNITED STATES PATENTS

| | | | |
|---|---|---|---|
| 1,327,114 | 1/1920 | Rhein................................. | 33/169 B |
| 3,058,225 | 10/1962 | Ward.................................. | 128/2 S |
| 3,239,938 | 3/1966 | Kaercher........................... | 33/172 E |
| 3,660,901 | 5/1972 | Inoue................................. | 128/2 S |

FOREIGN PATENTS OR APPLICATIONS

| | | | |
|---|---|---|---|
| 1,210,417 | 9/1959 | France ............................ | 33/172 E |
| 26,188 | 8/1970 | Japan............................... | 33/172 E |
| 1,548,266 | 1/1970 | Germany........................... | 33/172 E |

*Primary Examiner*—Robert W. Michell
*Assistant Examiner*—Lee S. Cohen
*Attorney, Agent, or Firm*—Chernoff & Vilhauer

[57] ABSTRACT

An apparatus for the simultaneous measurement and remote recordation of the depth of the gingival sulci and other similar anatomical recesses. The apparatus comprises a periodontal depth probe with a protruding, removably-attached cylindrical probe tip partially ensheathed by a slideable tubular sleeve which is electrically connected via a transducer within the probe body to a remote recording device. Translational movement of the slideable tubular sleeve partially sheathing the probe tip varies an electrical signal between the probe and the remote recording device according to the length of probe tip exposed. An operator-controlled foot switch is connected between the probe and the remote recording device to allow the operator to insert the probe tip into the gingival sulcus and adjust the slideable sleeve until it touches the margin of the gingiva before actuating the remote recording device. When activated, the recorder produces a record of the electrical signal corresponding to the length of the exposed probe tip and thus representative of the depth of the gingival sulcus at the measured location. In one embodiment the movement of the slideable sleeve is converted into an electrical signal by proportionately exposing a light-sensitive circuit element, such as a photocell, to a fixed intensity light source enclosed in the probe handle. In a second embodiment the slideable sleeve is attached to an electrical contact point that is in movable contact with a series of fixed contact points or taps, each of which corresponds to a discrete length of exposed (unsleeved) probe tip. The remote recording device converts the electrical signals from either embodiment into a permanent record as well as a visual display of the measured sulcus depth at the various tooth locations.

15 Claims, 11 Drawing Figures

REMOTE-RECORDING PERIODONTAL DEPTH PROBE

BACKGROUND OF THE INVENTION

This invention relates to a portable, hand-held depth indicator of the type generally used by dentists to measure the depths of the gingival sulci. The gingival sulci are the spaces between the gingival tissues (gums) and the teeth. The depth of each gingival sulcus is measured from the margin of the gingiva (top of the gum) to the epithelial attachment (point where the gum attaches to the tooth). With the two most common diseases of the gums and teeth supporting structures, gingivitis (inflamation of the gums) and advanced periodontal disease (sometimes called pyorrhea), the gums become swollen and begin to stand away from the teeth. If not treated early enough, the gums may actually withdraw from the teeth, forming pockets which may become filled with bacteria and pus, and result in the eventual destruction of the attachment of the teeth to the supporting bone structure. Advanced periodontal disease has been estimated to cause more adult tooth loss then the more common dental caries (cavities).

The most effective protection against gingivitis and advanced periodontal disease is early detection of any change in the gingival sulci by the periodical measurement and recordation of the sulcus depths at various locations around each tooth. A common instrument often used for this purpose is a depth probe, similar to that disclosed in Ward U.S. Pat. No. 3,058,225, comprising a handle with a fixed protruding sheath and a cylindrical probe tip extendable through the sheath and attached either directly to a mechanical indicator or indirectly, via electrical circuitry, to a current indicating device located on the probe handle. The major disadvantage with this conventional type of probe is that, to measure a sulcus depth, the sheath is rested on the margin of the gingiva while the probe tip is extended into the sulcus until it reaches the epithelial attachment. With such a probe the probe tip is not visible to the dentist as it is extended into the sulci and, if extended too far, may inadvertently penetrate or tear the epithelial attachment. In addition, since the depth measurement is indicated on the probe handle itself, the dentist must either measure and then record the individual measurements himself by hand, or employ an assistant to do the recording as the dentist calls out the measurements. Also, with the indicator on the handle itself, it is sometimes awkward or impossible, depending upon the location of the sulcus being measured, to read and record the measurement without removing the probe from the patient's mouth, thereby risking a disturbance of the measurement and a resulting erroneous reading. Since the normal mouth has from twenty-eight to thirty-two teeth and each tooth requires approximately six measurements, the time wasted by the separate measurement and recordation of each sulcus depth is considerable. Even if the electrical current indicating device is removed from the probe handle and placed where it can be more easily read, as suggested by Ward, the dentist must still stop and record each individual measurement himself or employ an assistant to do so.

SUMMARY OF THE PRESENT INVENTION

The present invention is directed to an apparatus for simultaneously measuring and remotely recording the depth of the gingival sulci and, more particularly, to an apparatus employing a hand-held periodontal depth probe electrically connected to a remote recording device capable of producing a permanent visual record of the sulcus depth being measured whenever an operator-controlled foot pedal is depressed. The probe itself comprises a cylindrical-shaped body with a substantially rigid, removably-attached probe tip protruding from one end and a multi-conductor electrical cable emanating from the other. Partially sheathing the probe tip, beginning at the point where it attaches to the probe body, is a longitudinally-movable, tubular sleeve of flexible material slideably attached to the probe body. This slideable sleeve is, in turn, connected to a transducer within the probe body capable of converting the translational movement of the sleeve relative to the probe into an electrical signal. Attached to the movable sleeve is a finger rest to facilitate the movement of the sleeve forward and backward over the probe tip with one finger.

By using a probe with a fixed probe tip and a movable sleeve, in contradistinction to the prior art probe design which employs a fixed sleeve and a movable probe tip, there is considerably less danger of accidentally penetrating or tearing the epithelial attachment as the probe tip is inserted into the gingival sulcus. With the present invention the probe tip remains visible to the operator while it is inserted into the sulcus until it touches the epithelial attachment. Only then is the sleeve moved forward along the probe tip until it comes in contact with the margin of the gingiva. By inserting the probe tip first in its unsheathed condition, not only is there less chance of injury to the patient, but the probe is easier to place and hold in position while the measurement is being recorded. This is especially true when measuring the sulci around the molars where the various measuring points are difficult to reach.

Both the probe tip and the movable sleeve are replaceable and can be detached from the probe for sterilization after each use. While a used tip and sleeve are being sterilized, a clean tip and sleeve can be attached and the probe re-used. In this manner, a single remote recording probe system can be used to measure the sulci of more than one patient with a minimum of delay between each use.

The multi-conductor cable from the probe body is connected to a moving-medium type recorder, such as a chart or strip recorder, capable of creating a permanent visual record of an input signal via electronic circuitry contained within the recorder enclosure. This electronic circuitry converts the electrical signal from the probe transducer into a second electrical signal, representing the length of exposed probe tip unsheathed by the movable sleeve, and also controls the actions of the recorder itself. Depending upon the recorder employed, the permanent record can be in either analog or digital form similar to that produced by a standard chart recorder or a small paper-tape adding machine respectively. Connected to the recorder control circuitry is an operator-controlled foot switch that is depressed by the probe operator each time it is desired to record the sulcus depth being measured by the probe. One mark or record is made each time the foot pedal is depressed. Thus, the probe operator need merely insert the probe tip into the sulcus, move the sleeve forward, and then depress the foot pedal to obtain an accurate measurement of the sulcus depth. There is no need for the operator to hand record each measurement or to employ an assistant to do so. The recording medium is automatically advanced after each record and the measuring process may be interrupted and restarted as necessary. By using preprinted forms and following a prescribed sequence of measurements of the patient's teeth, each recorded depth measurement may be readily and automatically associated with the tooth location of the point being measured.

It is therefore a primary objective of the present invention to provide an apparatus for simultaneously and automatically creating a permanent and visible record of the depth of each gingival sulcus as it is measured.

It is a further objective of the present invention to provide a safe means for measuring the depth of the gingival sulci by utilizing a periodontal depth probe the tip of which is fully visible to the operator while it is being inserted into each sulcus.

It is an additional objective of the present invention to provide an apparatus for measuring and recording the depth of gingival sulci at numerous and various locations in a patient's mouth which can be conveniently used by a single unassisted operator.

It is a principal feature of the present invention that the components of the periodontal depth probe that come in contact with a patient are detachable so that they can be readily removed and replaced with sterilized components after each use.

It is a primary advantage of the present invention that accurate and safe measurements of individual gingival sulcus depth can be made even around those teeth that are difficult or awkward to reach with the measuring probe.

The foregoing and other objectives, features, and advantages of the present invention will be more readily understood upon consideration of the following detailed description of the invention taken in conjunction with the accompanying drawings.

BRIEF DESCRIPTION OF THE DRAWINGS

FIG. 3B' is a sectional view of the rear half of a second embodiment of the depth probe assembly taken along line 3—3 of FIG. 2.

DESCRIPTION OF THE PREFERRED EMBODIMENT

Figure 1:
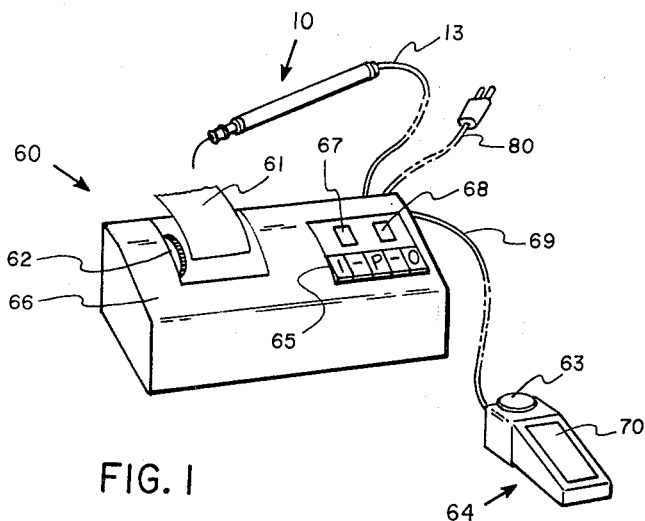
FIG. 1 is a perspective view of an illustrative embodiment of the periodontal depth probe and remote recorder instrument of the present invention.

Referring to the perspective view of FIG. 1, the preferred instrument embodiment of the present invention is seen to comprise a periodontal depth probe assembly 10, remote recording console 60, operator foot switch 64, and their respective associated electrical conduits 13, 69 and 80 connecting the console to the probe, the foot switch and a source of AC electrical potential, respectively. Depth probe assembly 10, as shown in the perspective view of FIG. 2 and the partial sectional view of FIG. 3, is seen to comprise a tubular metal probe body 11 generally cylindrical in form and having a partially ensheathed probe tip 12 protruding from its forward end and electrical cable 13 attached to its rearward end. The forward end 14 of probe body 11 is diametrically reduced and externally threaded to receive knurled probe tip retainer 15, and rearward end 16 is internally threaded to receive end cap 17.

Probe tip 12, protruding from the forward end of probe body 11, comprises a length of substantially rigid metal rod, preferably of stainless steel, with an arcuate forward extremity rounded at its tip and a right angle circular loop 25 formed at its rear for snap-in spring engagement by the interior retainer cap 15 which in turn is screwed on to the forward end 14 of the probe body. The probe tip can be readily detached for sterilization or replacement by unthreading the retainer 15 and partially disassembling the probe as described later.

Slideably engaged in the forward bore 18 of probe body 11 is connecting tube 19, comprising a cylindrical tube diametrically reduced and externally threaded at its forward end 20 to receive finger rest 21. Formed along the axis of connecting tube 19 is bore 22, the rearward portion of which is diametrically larger than the forward portion to allow the insertion and retention of resilient friction tube 23. Formed along the forward length of connecting tube 19 is longitudinal slot 24 allowing limited reciprocal movement of connecting tube 19 past probe tip 12. Forward movement of connecting tube 19 is limited by the stop formed by the rear wall 26 of slot 24 striking probe tip 12 and rearward movement is limited by rear wall 27 of forward probe body bore 18.

Finger rest 21, which serves to connect probe tip sleeve 28 to sleeve connecting tube 19 and to facilitate one-finger longitudinal adjustment of sleeve 28 over the protruding length of tip 12, is formed from solid metal, cylindrically-shaped stock internally bored and threaded at both ends and having a rearwardly tapering bore 29 connecting front bore 30 to rear bore 31. The outer surface of finger rest 21 is axially reduced toward the center to facilitate its positive reciprocal control by one finger.

Probe tip sleeve 28 comprises a length of flexible tubing, preferably of a relatively soft smooth plastic material to minimize risk of injury to tissue material which it contacts, the inside diameter of which is slightly larger than the diameter of probe tip 12. Inserted into the rearward orifice of sleeve 28 is metal support tube 32, the inside diameter of which is also slightly larger than the diameter of probe tip 12. Sleeve 28 is removably attached to finger rest 21, and thereby to connecting tube 19, by the frictional engagement of its rearward portion between resilient retainer ring 33 and support tube 32. Retainer ring 33 is held in tapered bore 29 of finger rest 21 and compressed against sleeve 28 by hollow retaining bolt 34 which is screwed into forward threaded bore 30 of finger rest 21. Sleeve 28 is prevented from collapsing under the compressive force of retainer ring 33 by support tube 32 which is flanged at its rearward end to allow easy insertion and removal.

Connecting tube 19 is attached to connecting rod 35 via the frictional engagement of forward diametrically-reduced portion 36 of connecting rod 35 by friction tube 23 seated in the rearward orifice of bore 22 of connecting tube 19. Thus, any longitudinal movement of probe tip sleeve 28 is transferred into a similar longitudinal movement of connecting rod 35 and this in turn is converted into a corresponding electrical signal by a suitable mechano-electrical motion transducer located in the rear handle portion of the probe body 11. In addition, the frictional connecting between connecting tube 19 and connecting rod 35 allows the sleeve retaining assembly, and thereby the probe tip, to be removed and replaced, as necessary, simply by unscrewing retainer cap 15 from the probe body and disengaging tube 19 from rod 35.

Figure 3A:
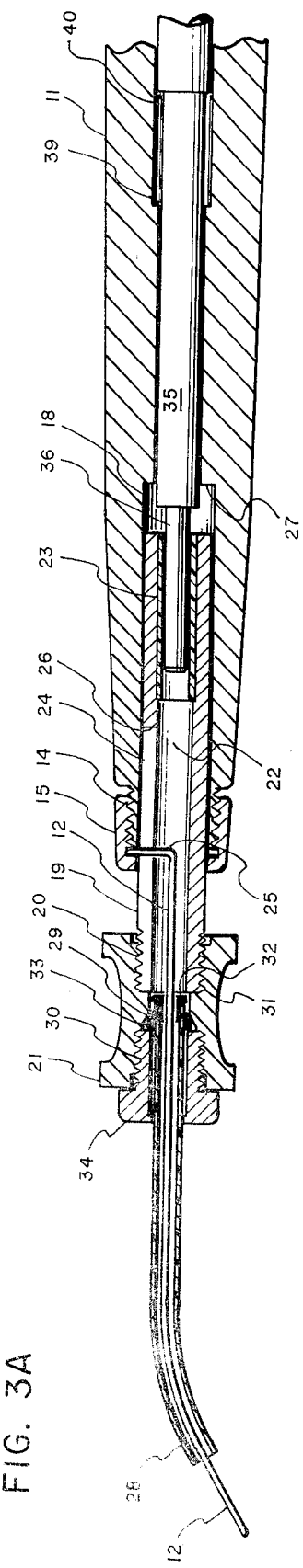
FIG. 3A is a sectional view of the front half of the depth probe assembly of the present invention taken along line 3—3 of FIG. 3.
Figure 3B:
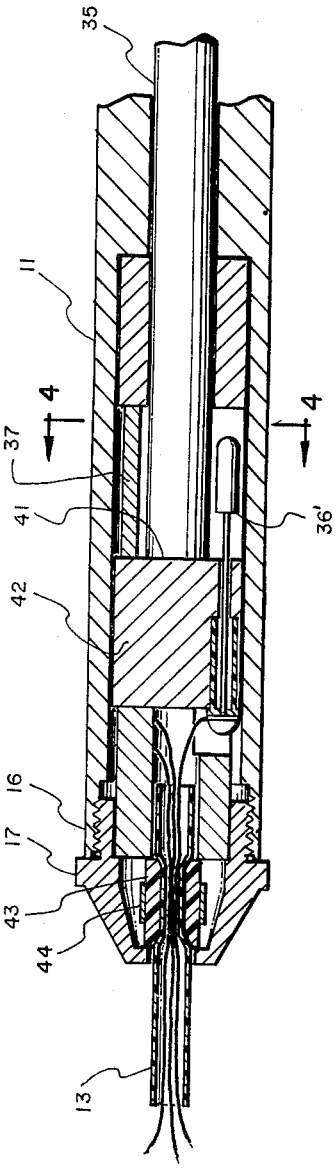
FIG. 3B is a sectional view of the rear half of the preferred embodiment of the depth probe assembly of the present invention taken along line 3—3 of FIG. 2.
Figure 4:
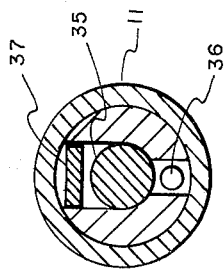
FIG. 4 is a detail sectional view taken along line 4—4 of FIG. 3B.
Figure 5:
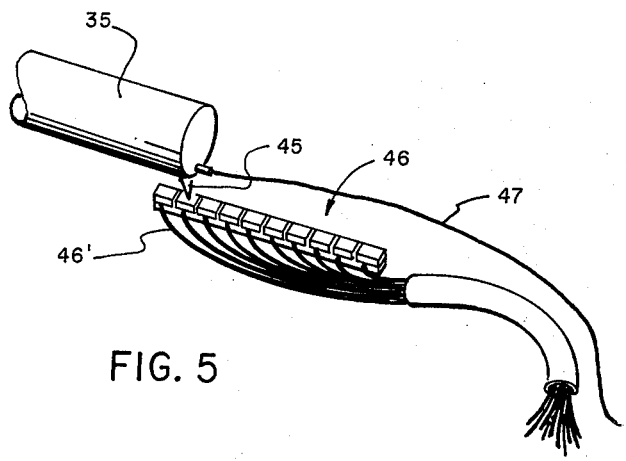
FIG. 5 is a detail perspective view of the multi-contact switch shown in the probe embodiment of FIG. 3B'.

In one embodiment, shown in the sectional views of FIGS. 3B and 4, the rear portion of connecting rod 35 serves as a movable shield between a fixed intensity light source 36' and photoelectric cell 37. When probe tip sleeve 28 is moved forward, thereby moving connecting rod 35 forward, a proportionate area of photoelectric cell 37 is exposed to the light source. The resultant electrical signal produced by the photoelectric cell is carried from the probe body, and power for light source 36' is supplied to the probe, by respective conductors in cable 13. The forward movement of connecting rod 35 is limited, as shown in FIG. 3A, by the stop formed by annular bore shoulder 39 and annular rod shoulder 40 whereas rearward movement is limited by the forward face 41 of the light source support 42. Cable 13 is protected from accidental extraction from probe body 11 by frictional engagement with grommet 43 which is compressed against the cable by annular clip 44 and restrained from movement by end cap 17.

In an alternate embodiment of the present invention, shown in FIGS. 3B' and 5, instead of the photocell transducer arrangement of FIG. 3B the rear extremity of connecting rod 35 includes fixedly-attached contact point 45 in movable electrical communication with a series of spaced stationary contact points or taps 46 which are connected respectively by thin wire leads 46' to discrete incremental levels of externally-supplied votage potential. A total of ten separate voltage level taps 46 are shown; however, more could be employed if desired to increase the resolution of the instrument. As probe tip sleeve 28 is longitudinally positioned along probe tip 12, movable contact point 45 is sequentially brought into electrical communication with respective ones of the stationary taps, thereby impressing a corresponding voltage level onto conductor 47 representing the length of probe tip then exposed. Conductor 47, as well as the conductors to the individual stationary contacts, are routed from probe body 11 via cable 13 which is frictionally retained in the orifice of end cap 17 by resilient grommet 43'.

Although only two forms of motion transducers for converting the translational position of probe tip sleeve 28 into an electrical signal representative of the exposed length of probe tip 12 are shown, it is to be understood that other transducer means known to the art could be coupled to the connecting rod 35 for this purpose, such as for example, a precision slidewire rheostat, a stationary inductor coil with a movable powdered iron core inserted therein, or a pair of stationary capacitor plates with a movable dielectric plate placed therebetween.

Figure 6:
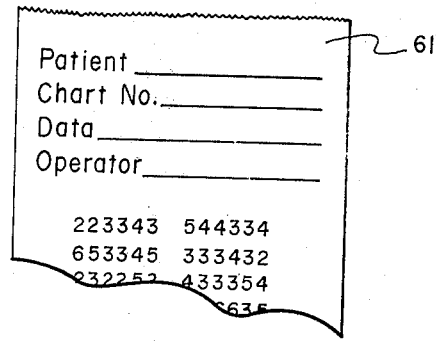
FIG. 6 shows a segment of the printed tape output from the recording device of the instrument embodiment of FIG. 1.
Figure 6A:
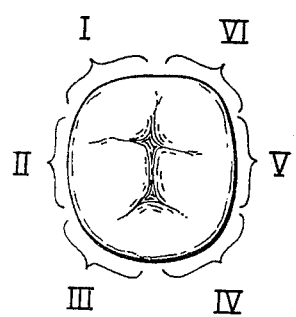
FIG. 6A is a top view of a mandibular molar showing the six areas usually probed around each tooth in the mouth.

The remote recorder console 60, shown in FIG. 1, converts the analog voltage signal from the transducer in the probe assembly into a digital signal corresponding to the length of exposed probe tip 12. The recorder section of the console 60 in turn converts this digital signal into a permanent visual record such as paper tape 61. Referring to the segment of the paper tape record 61 shown in FIG. 6, the first group of six numerals in a horizontal row printed indicate, illustratively in millimeters, six depth measurement recordings made at spaced locations around a single tooth, as depicted in FIG. 6A. Each succeeding group of six printed numerals similarly represent depth measurements made on other teeth. The tape record can be advanced, either manually by thumb wheel 62 or one line at a time by depressing button switch 63 of foot control 64 or control tab 65 on the console. Automatic spacing and tape advance would typically be provided the printer after each group of six measurements and as each row on the tape is completed.

Also included on the panel 66 of the console is position indicator 67 and depth measurement display 68. Position indicator 67 is a counter indicating the point, in a preselected sequence of measurements to be made by the operator at predetermined tooth locations in the mouth of a patient, at which the current measurement is being made. This is very useful if the operator should be interrupted in his sequence of measurements. Measurement display 68 provides a digital display of the length of probe tip currently exposed so that the operator has available for convenience of reference a reading of the depth measurement as it is being made. Pedal 70 on foot switch 64 is depressed whenever it is desired to make a permanent record of the value displayed by depth indicator 68. Although a digital recording device is indicated in FIG. 1, it is to be understood that an analog recording device, such as a strip or chart recorder, could also be employed without departing from the principles of the present invention.

Figure 2:
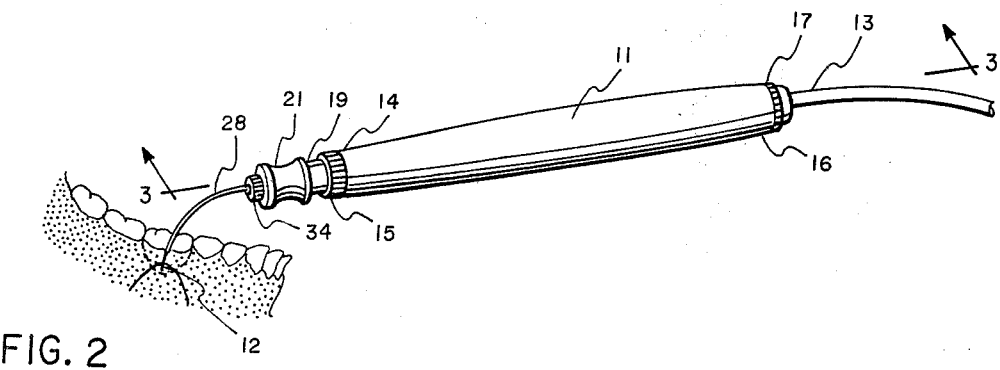
FIG. 2 is an enlarged perspective view of the periodontal depth probe assembly.
Figure 7:
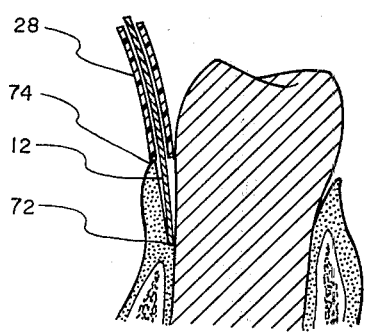
FIG. 7 is a sectional view illustrating the sleeve of the probe tip inserted and adjusted to measure the depth of the gingival sulcus of a tooth.
Figure 3B:
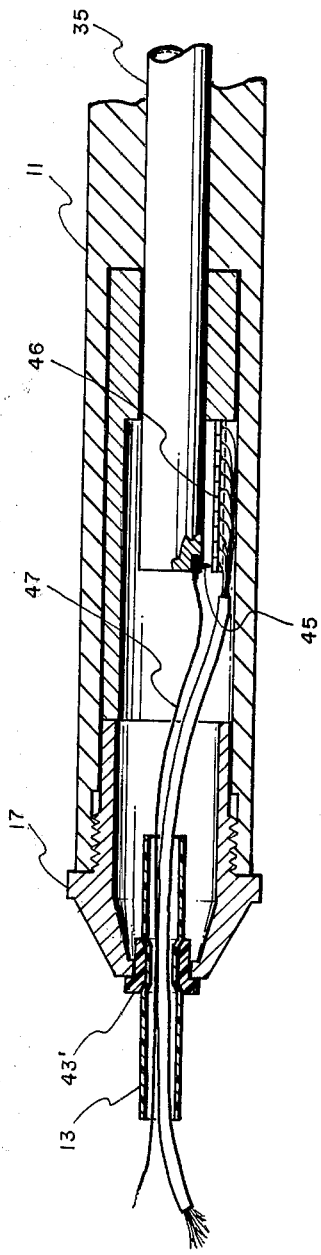

In use, to measure and record the depth of the gingival sulci around a particular tooth, finger rest 21 is retracted to its far rearward position near probe tip retainer 15, and probe tip 12 is gently inserted into the sulcus, as shown in FIGS. 2 and 7, until the tip extremity comes in contact with gingival attachment 72. Finger rest 21 is then moved forward until probe tip sleeve 28 touches the margin of the gingiva 74. The length of probe tip exposed now corresponds directly to the depth of the sulcus, as measured from the margin of the gingiva to the gingival attachment. As probe tip 12 is inserted and finger rest 21 is being positioned, the length of unsheathed probe tip is being continuously displayed by depth display 68 on the recorder console 60. When the operator is satisfied with the placement and adjustment of the probe, pedal 70 on the foot switch 64 is momentarily depressed, causing the measured depth to be recorded on tape medium 61 and position indicator 67 to be advanced to its next position. Thus, any number of depth measurements may be made and recorded without need for withdrawing the depth probe from the patient's mouth.

Figure 8:
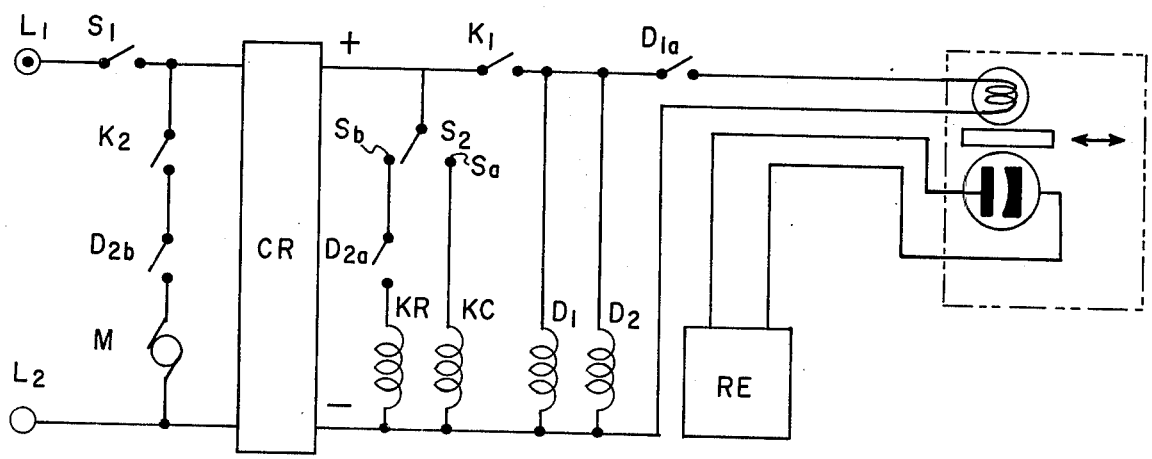
FIG. 8 is a schematic diagram of an exemplary strip chart recorder control circuit which may be employed with the remote recorder instrument of the present invention.

FIG. 8 is a schematic diagram of a circuit that may be used to control an analog strip recorder when such a recorder is employed as the recording means for the depth probe of the present invention. In the diagram, the rectangle labeled CR represents a voltage dropping and current rectifying circuit while the rectangle RE represents the drive mechanism for the recording stylus. Lamp 36, slideable connecting rod 35, which acts as a light shield, and photocell 37, while included in the schematic, are actually located in the body of the probe as described previously.

The initial conditions for the circuit are as shown in the diagram with contact S*b* of single-pole double-throw switch S2 closed, relay contacts K1 and K2 open, delay contacts D1*a* and D2*a* closed and delay contact D2*a* open. Standard AC power is applied to the circuit via terminals L1 and L2 when switch S1 is closed.

To record a depth measurement, the probe is positioned and adjusted as described earlier so that the unsheathed portion of probe tip 12 represents the depth to be recorded. When the probe is so positioned and adjusted, the pole of switch S2, preferably located in an operator-controlled foot switch, is thrown from contact S*b* to contact S*a*, thereby energizing relay coil KC. With relay coil KC so energized, relay contacts K1 and K2 close to supply power to lamp 36 and chart drive motor M. Once closed, contacts K1 and K2 are locked by mechanical means. Connecting rod 35, because of its connection with probe tip sleeve 28, will be positioned to allow an amount of light corresponding to the length of unsheathed probe tip to reach photocell 37 causing an electrical signal to be generated and the recording stylus drive mechanism RE to be activated accordingly. Thus, as long as relay contacts K1 and K2 remain closed, the chart will be moved and a line will be drawn thereon representing the magnitude of the depth being measured.

The closing of relay contact K1 also energizes delay coils D1 and D2. A fixed period of time after delay coil D2 has been energized, delay contacts D1*a* and D2*b* will open, thereby disconnecting power from both lamp 36 and chart motor M. At a longer period of time after delay coil D1 has been energized, delay contact D2*a* will then close. Assuming that the movable pole of foot switch S2 was only momentarily moved to contact S*a* and has since been returned to contact S*b*, the closing of delay contact D2*a* will energize relay coil KR which in turn will release the mechanical lock holding relay contacts K1 and K2 closed, allowing those contacts to open. The opening of relay contact K1 deenergizes delay coils D1 and D2 allowing all delay contacts, and thereby the remainder of the circuit, to return to their initial positions. This sequence is repeated each time the movable pole of S2 is momentarily moved from contact S*b* to contact S*a* or, in other words, whenever the probe operator momentarily depresses the foot switch.

The terms and expressions which have been employed in the foregoing abstract and specification are used therein as terms of description and not of limitation, and there is no intention, in the use of such terms and expressions, of excluding equivalents of the features shown and described, or portions thereof, it being recognized that the scope of the invention is defined and limited only by the claims which follow.

What is claimed is:

1. An apparatus for simultaneously measuring and remotely recording the depth of an anatomical recess comprising:
   a. a hand-held depth probe body;
   b. a substantially rigid, arcuate probe tip attached to said body for insertion into said recess;
   c. a probe tip sleeve partially ensheathing said probe tip and slidably movable relative thereto for contact with the edge of said recess, said sleeve being of flexible material so as to permit said sleeve to conform to the arc of said probe tip as said sleeve is moved therealong;
   d. transducer means for converting the position of said probe tip sleeve relative to said probe tip into a signal representing the depth of said recess;
   e. means for converting said signal into a permanent record and visual display of said depth; and
   f. means for actuating said signal conversion means on command to produce said record of said depth.

2. The apparatus of claim 1 wherein said transducer means comprises a mechano-electrical transducer located within said probe body and in communication with said slideable probe tip sleeve for converting the position of said probe sleeve relative to said probe tip into an electrical signal representative thereof.

3. The apparatus of claim 2 wherein said mechano-electrical tranducer comprises:
   a. a fixed intensity light source;
   b. a photocell opposed said light source for generating an electrical signal whose amplitude is responsive to the amount of radiation incident thereon from said light source; and
   c. a movable light shield between said light source and said photocell and in communication with said probe tip sleeve so that movement of said probe tip sleeve relative to said probe tip varies the area of said photocell exposed to said light source.

4. The apparatus of claim 2 wherein said mechano-electrical transducer comprises:
   a. a plurality of fixed electrical contacts each connected to respective incremental voltage levels; and
   b. a movable electrical contact in communication with said probe tip sleeve and sequentially with said fixed contacts so that movement of said probe sleeve relative to said probe tip sequentially connects said movable contact to said respective voltage levels.

5. The apparatus of claim 1 wherein said signal conversion means comprises movable-media chart recorder means for converting said signal into a permanent visual record of said measurement.

6. The apparatus of claim 1 wherein said signal conversion means includes both printer means for converting said signal into a printed indicia representative of the value thereof onto a recording medium and display means for indicating the instantaneous value of said signal.

7. The apparatus of claim 1 wherein said actuating means includes an operator-controlled foot switch.

8. The apparatus of claim 1 wherein said signal conversion means is located at a remote position from said depth probe body and said transducer means.

9. An improved hand-held depth probe of the type used to measure the depth of an anatomical recess wherein said depth is determined by the distance between the extremity of a probe tip inserted into said recess and the extremity of a probe tip sleeve partially ensheathing said probe tip and resting on the edge of said recess, wherein the improvement comprises:
  a. an arcuate probe tip fixedly connected to the body of said depth probe; and
  b. a probe tip sleeve slidably attached to said probe body and consisting essentially of flexible material so as to permit said sleeve to conform to the arc of said probe tip, whereby said probe tip can be fully inserted into the depth of said recess and held with said probe tip body at an angle offset from the angle of the depth dimension of said recess while said probe tip sleeve is adjusted to rest on the edge of said recess.

10. The depth probe of claim 9 wherein said probe tip is detachably connected to said probe body for ready removal for sterilization or replacement when desired.

11. An apparatus for simultaneously measuring and remotely recording the depth of an anatomical recess comprising:
  a. means for measuring the depth of said anatomical recess;
  b. transducer means for converting the depth measurement obtained by said measuring means into a signal representing said measurement;
  c. means for converting said signal into a permanent record and visual display of said depth measurement;
  d. means for actuating said signal conversion means on command to produce said record of said depth measurement; and
  e. counter means for displaying the number of recorded depth measurements made from the start of a sequence of such measurements.

12. The apparatus of claim 11 wherein said signal conversion means includes printer means for recording and displaying a digital representation of said measurement on an elongate strip of paper tape.

13. The apparatus of claim 12 wherein said printer means includes means for displaying a sequence of said measurements in a group.

14. The apparatus of claim 11 wherein said signal conversion means includes chart recorder means for recording an analog representation of said measurements on a movable medium.

15. The apparatus of claim 11 wherein said signal conversion means includes digital means for displaying a numerical representation of the exposed length of said probe tip.

* * * * *

UNITED STATES PATENT AND TRADEMARK OFFICE
CERTIFICATE OF CORRECTION

PATENT NO. : 3,943,914
DATED : March 16, 1976
INVENTOR(S) : James W. Grenfell, Fred M. Sorenson, Hiroshi Ueno, Masato Miyahara It is certified that error appears in the above-identified patent and that said Letters Patent are hereby corrected as shown below:

Col. 2, Line 38      Change "replacable" to --replaceable--.

Col. 5, Line 54      Change "votage" to --voltage--.

Col. 7, Line 17      Change "D2a" to --D2b--.

Col. 10, Lines 23-24      Change "the exposed length of said probe tip" to --said depth measurement--.

Signed and Sealed this

Thirty-first Day of August 1976

[SEAL]

Attest:

RUTH C. MASON
*Attesting Officer*

C. MARSHALL DANN
*Commissioner of Patents and Trademarks*